US006476281B2

(12) United States Patent
Qian et al.

(10) Patent No.: US 6,476,281 B2
(45) Date of Patent: Nov. 5, 2002

(54) METHOD FOR THE PREPARATION OF 1,1,1,3,3-PENTAFLUOROPROPENE AND 1,1,1,3,3-PENTAFLUOROPROPANE

(75) Inventors: John Cheng-Ping Qian, El Dorado, AR (US); Julia Ann Sacarias, El Dorado, AR (US)

(73) Assignee: PCBU Services, Inc., Wilmington, DE (US)

( * ) Notice: Subject to any disclaimer, the term of this patent is extended or adjusted under 35 U.S.C. 154(b) by 0 days.

(21) Appl. No.: 09/915,630

(22) Filed: Jul. 26, 2001

(65) Prior Publication Data

US 2002/0002314 A1 Jan. 3, 2002

Related U.S. Application Data

(63) Continuation of application No. 09/286,150, filed on Apr. 5, 1999.
(51) Int. Cl.⁷ .............................................. C07C 17/25
(52) U.S. Cl. ....................................... 570/156; 570/157
(58) Field of Search ................................ 570/156, 157, 570/176

(56) References Cited

U.S. PATENT DOCUMENTS

| 2,900,423 | A | 8/1959 | Smith ........................ 570/156 |
| 5,057,634 | A | 10/1991 | Webster et al. .............. 570/157 |
| 5,523,501 | A | 6/1996 | Kellner et al. ............... 570/159 |

FOREIGN PATENT DOCUMENTS

| EP | 0 703 207 A | 3/1996 |
| WO | WO 90 08748 A | 8/1990 |
| WO | WO 94/29251 | 12/1994 |
| WO | WO 98 37043 A | 8/1998 |
| WO | WO 98/37043 | 8/1998 |

OTHER PUBLICATIONS

Bull., Acad. Sci., USSR Div. Chem. Sci. (Eng. Trans.), 1312–1317 (1960).

J. Amer. Chem. Soc. 68, 496–497 (1946).

*Primary Examiner*—Alan Siegel
(74) *Attorney, Agent, or Firm*—Baker & Daniels

(57) ABSTRACT

A method for the production of 1,1,1,3,3-pentafluoropropene, and particularly to a method characterized by high conversion, yield and selectivity by contacting 2,2-dichloro-1,1,1,3,3,3-hexafluoropropane with hydrogen in the presence of a metal-containing catalyst. The 1,1,1,3,3-pentafluoropropene then can be reacted with hydrogen in the presence of a metal-containing catalyst to produce 1,1,1,3,3-pentafluoropropane.

27 Claims, No Drawings

METHOD FOR THE PREPARATION OF 1,1,1,3,3-PENTAFLUOROPROPENE AND 1,1,1,3,3-PENTAFLUOROPROPANE

CROSS-REFERENCE TO RELATED APPLICATION

This application is a continuation of U.S. application Ser. No. 09/286,150 filed Apr. 5, 1999.

BACKGROUND OF THE INVENTION

1. Field of the Invention

The present invention relates to a method for the production of 1,1,1,3,3-pentafluoropropene, and particularly to a method characterized by high conversion, yield and selectivity by contacting 2,2-dichloro-1,1,1,3,3,3-hexafluoropropane with hydrogen in the presence of a metal-containing catalyst. The 1,1,1,3,3-pentafluoropropene then can be reacted with hydrogen in the presence of a metal-containing catalyst to produce 1,1,1,3,3-pentafluoropropane.

2. Description of the Prior Art

Numerous methods are disclosed in the prior art for the preparation of 1,1,1,3,3-pentafluoropropene ($CF_3CH=CF_2$). These methods vary widely, due in part to the different starting materials involved. The present invention provides a novel method for the preparation of 1,1,1,3,3-pentafluoropropene via the treatment of 2,2-dichloro-1,1,1,3,3,3-hexafluoropropane ($CF_3CCl_2CF_3$) with hydrogen in the presence of a catalyst. The reaction is characterized by high selectivity, conversion and yield, and offers significant economic advantages over prior art preparations.

1,1,1,3,3-pentafluoropropene is a known chemical, and has found use as a valuable intermediate in the preparation of a variety of useful compounds. For example, as described in *Bull. Acad. Sci., USSR Div. Chem. Sci.* (Eng. Transl.), 1312 (1960) and in *Chemical Abstracts* 122:132564, treatment of 1,1,1,3,3-pentafluoropropene with hydrogen in the presence of a catalyst produces 1,1,1,3,3-pentafluoropropane, a compound useful as a solvent and blowing agent.

1,1,1,3,3-pentafluoropropene has been produced via the dehydrochlorination of 3-chloro-1,1,1,3,3-pentafluoropropane ($CF_3CH_2CF_2Cl$) with base as described in *J. Amer. Chem. Soc.* 68, 496 (1946).

1,1,1,3,3-pentafluoropropene has been prepared via dehydrofluorination of 1,1,1,3,3,3-hexafluoropropane with activated carbon or fluorinated chromium oxide (JP 09067281; Chem Abs. 126:277171), and via treatment of the potassium salt of 2-trifluoromethyl-3,3,3-trifluoropropionic acid with ethyl acetate as described in JP 08325179; Chem Abs. 126:143890).

1,1,1,3,3-pentafluoropropene has been prepared via dechlorination of 2,3-dichloro-1,1,1,3,3-pentafluoropropane ($CF_3CHClCF_2Cl$) with hydrogen in the presence of a metal oxide catalyst as described in WO 9429251.

WO 9837043 describes the treatment of 2,2-dichloro-1,1,3,3,3-hexafluoropropane ($CF_2CCl_2CF_3$) with hydrogen in the presence of a metal, metal halide or metal oxide catalyst supported or alumina or a metal fluoride to produce a mixture of 1,1,1,3,3-pentafluoropropene and 2-chloro-1,1,1,3,3-pentafluoropropene ($CF_3CCl=CF_2$).

Selectivity to $CF_3CH=CF_2$ is low, with substantial amounts of the chlorine-containing olefin $CF_3CCl=CF_2$ being co-produced in all cases.

Although the above described methods serve to produce 1,1,1,3,3-pentafluoropropene, these prior art preparations are characterized by numerous disadvantages, including expensive raw materials, poor yields and poor selectivity which preclude their use on a commercial scale.

SUMMARY OF THE INVENTION

Briefly describing one aspect of the present invention, there is provided a method for the production of 1,1,1,3,3-pentafluoropropene which includes reacting 2,2-dichloro-1,1,1,3,3,3-hexafluoropropane and hydrogen at elevated temperature in the presence of a catalyst, and thereafter recovering the resulting 1,1,1,3,3-pentafluoropropene from the reaction mixture.

It is an object of the present invention to provide a method for the production of 1,1,1,3,3-pentafluoropropene from readily available starting materials. The starting material 2,2-dichloro-1,1,1,3,3,3-hexafluoropropane is itself a known compound, and is readily produced in high yields via the treatment of propane or propene with chlorine and hydrogen fluoride as described in U.S. Pat. No. 5,057,634, hereby incorporated by reference.

A further object of this invention is to provide a method which has high conversion, high yield and high selectivity for the desired product, 1,1,1,3,3-pentafluoropropene.

It is another object of the present invention to provide a method as described which does not produce significant amounts of undesirable by-products.

Further objects and advantages of the present invention will be apparent from the description of the preferred embodiment which follows.

DESCRIPTION OF THE PREFERRED EMBODIMENTS

For the purposes of promoting an understanding of the principles of the invention, reference will now be made to the preferred embodiment and specific language will be used to describe the same. It will nevertheless be understood that no limitation of the scope of the invention is thereby intended, such further modifications in the invention, and such further applications of the principles of the invention being contemplated as would normally occur to one skilled in the art to which the invention relates.

The present invention is based upon the discovery that 1,1,1,3,3-pentafluoropropene may be produced via the reaction of 2,2-dichloro-1,1,1,3,3,3-hexafluoropropane and hydrogen at elevated temperatures in the presence of a catalyst. The conversions and selectivities for this process are very high, rendering the process applicable to commercial scale production.

The basic method of the present invention involves the reaction of 2,2-dichloro-1,1,1,3,3,3-hexafluoropropane and hydrogen in the presence of a catalyst, preferably a metal-containing catalyst, according to the following reaction (I):

$$CF_3CCl_2CF_3 + 2H_2 \rightarrow CF_3CH=CF_2 + HF + 2HCl \qquad (I)$$

The reaction (I) is carried out by contacting 2,2-dichloro-1,1,1,3,3,3-hexafluoropropane and hydrogen at elevated temperatures in the presence of a catalyst. Although preferred ranges for contact times and molar ratios are stated hereafter, these ranges are not critical. In addition, the reaction may be carried out at ambient or elevated pressures.

The temperature of the reaction is generally one which is high enough to provide a desired amount and rate of conversion of the 2,2-dichloro-1,1,1,3,3,3-hexafluoropropane, and low enough to avoid deleterious effects such as the production of decomposition products.

The reaction is therefore preferably carried out at a temperature between about 100° C. and about 800° C. A more preferred range for the reaction is about 300° C. to about 500° C. It will be appreciated that the selected temperature for the reaction will depend in part on the contact time employed, in general, the desired temperature for the reaction varying inversely with the contact time for the reaction.

The contact time will vary depending primarily upon the extent of conversion desired and the temperature of the reaction. The appropriate contact time will, in general, be inversely related to the temperature of the reaction and directly related to the extent of conversion of 2,2-dichloro-1,1,1,3,3,3-hexafluoropropane.

The reaction will typically be conducted as a continuous flow of reactants through a heated reaction vessel in which heating of the reactants may be very rapidly effected. Under these circumstances, the residence time of the reactants within the vessel is desirably between about 0.1 second and 200 seconds, and is preferably about 10 seconds. An advantage of the reaction is that short contact times may be employed, thereby reducing the equipment size and cost associated with producing 1,1,1,3,3-pentafluoropropane. The reactants may be preheated before combining or may be mixed and heated together as they pass through the vessel. Alternatively, the process may be carried out in a batch process with contact time varying accordingly, although this is less preferred. The reaction also can be carried out in a multistage reactor, wherein gradients in temperature, mole ratio, or both temperature and mole ratio are employed.

The molar ratio of the reactants may vary widely and is not critical to the inventive method. Limitations on this ratio are more determined by practical considerations. For example, a molar ratio of hydrogen to 2,2-dichloro-1,1,1,3,3,3-hexafluoropropane which is extremely low will simply require greater recycle of the 2,2-dichloro-1,1,1,3,3,3-hexafluoropropane due to the low conversion, whereas a ratio that is very high will be wasteful of hydrogen. A preferred range for the molar ratio of hydrogen to 2,2-dichloro-1,1,1,3,3,3-hexafluoropropane is between about 0.1 and 30, with a ratio of about 2 to 8 being more preferred.

The invention provides a process for producing 1,1,1,3,3-pentafluoropropene using 2,2-dichloro-1,1,1,3,3,3-hexafluoropropane and involves the use of advantageous, preferred catalytic components employing a metal catalyst. The metal catalyst preferably is selected from the group consisting of a metal, metal oxide, metal halide, metal oxyhalide, and mixtures thereof, on a support, preferably a carbon support. Suitable metal-containing components include metals such as Fe, Cu, Ni and Cr; halides such as $FeCl_2$, $FeCl_3$, CuF, CuCl, $CuCl_2$, CuClF, $NiF_2$, $NiCl_2$, NiClF, $CrF_3$, $CrFCl_2$, $CrF_2Cl$; oxides such as CuO, NiO, and $Cr_2O_3$; and/or oxyhalides such as copper oxyfluoride and chromium oxyfluoride.

The catalysts of this invention may contain other components, some of which improve the activity and/or useful life of the catalyst. Preferred catalysts include catalysts which are promoted with compounds of molybdenum, vanadium, tungsten, silver, iron, potassium, cesium, rubidium, barium or combinations thereof.

The catalyst preferably is supported on an active carbon support. The active carbon can take the form of any of the numerous active carbons available commercially, for example the commercial guide product produced by Takeda. Typically the solid catalyst is packed into a reactor tube, although fluidized bed technology can also be employed.

The process of the present invention has several advantageous aspects in addition to those described above. The reaction involves readily obtainable reactants, namely 2,2-dichloro-1,1,1,3,3,3-hexafluoropropane and hydrogen. The reaction product is the desired 1,1,1,3,3-pentafluoropropene. Very high yields of the desired product are ultimately attainable, and therefore the reaction is efficient in its use of the reactants without producing miscellaneous undesirable by products, and is a highly efficient and advantageous method for the production of 1,1,1,3,3-pentafluoropropene.

The 1,1,3,3-pentafluoropropene product is separated from the product mixture via conventional means, for example distillation. The reaction stream can be treated with water or an aqueous solution to facilitate removal of inorganic acids, and the organic portion of the product mixture can be subjected to fractional distillation to allow recovery of the product and recycle of the starting material 2,2-dichloro-1,1,1,3,3,3-hexafluoropropene.

The efficacy of the process of the present invention is illustrated by the following specific examples. The following specific embodiments are to be construed as illustrative, and not as constraining the remainder of the disclosure in any fashion whatsoever.

EXAMPLE 1

Catalyst Preparation

NiO/active carbon: Nickel (II) nitrate hexahydrate (1.9 moles) was dissolved in distilled water (250 mL). The solution was then added to 550 g of Takeda active carbon pellets, the catalyst dried with nitrogen and activated at 450° C.

NiO/CuO/active carbon: A mixture of nickel (II) nitrate hexahydrate (0.95 mole) and copper (II) nitrate hemipentahydrate (0.95 mole) was dissolved in distilled water (320 mL). The solution was added to 500 g of active carbon pellets. The catalyst was then dried with nitrogen and activated at 450° C.

$CuCl_2$/active carbon: Copper (II) chloride dihydrate (1.9 moles) was dissolved in distilled water (325 mL). The solution was then added to 550 g of active carbon pellets. The catalyst was then dried with nitrogen and activated at 350° C. with hydrogen.

EXAMPLE 2

Preparation of 1,1,1,3,3-pentafluoropropene

A 10 inch diameter by 24 inch long Inconel pipe was packed with the desired catalyst and heated with an electric heater. A 0.5 inch by 8 inch empty pipe heated by electrical heating tape was connected to the inlet of the reactor and served as a vaporizer. A water scrubber and a molecular sieve drier were attached to the reactor outlet and were employed to remove acids from the product mixture and to dry the organic products. Hydrogen gas (200 mL/min) and liquid 2,2-dichloro-1,1,1,3,3,3-hexafluoropropane (0.3 mL/min) were fed into the vaporizer and the vaporized mixture passed through the reactor. The product mixture was washed with water, dried and collected. Reaction results are summarized in Table 1; the conversion of 2,2-dichloro-1,1,1,3,3,3-hexafluoropropane was essentially quantitative.

TABLE 1

Preparation of 1,1,1,3,3-pentafluoropropene

| Catalyst | Reaction T (° C.) | % Selectivity CF$_3$CH=CH$_2$ |
|---|---|---|
| NiO/CuO | 350 | 89 |
| NiO/CuO | 500 | 90 |
| NiO | 350 | 81 |
| NiO | 425 | 80 |
| CuCl$_2$ | 350 | 90 |

EXAMPLE 3

Preparation of 1,1,1,3,3-pentafluoropropane

A 0.5 inch by 24 inch stainless steel pipe was packed with a catalyst consisting of 0.5% Pd on alumina pellets and heated with an electric heater. A mixture of hydrogen (128 mL/min) and 1,1,1,3,3-pentafluoropropene, prepared as in Example 2, was fed to the reactor. The product stream was washed with water to remove acids and collected. Results are shown in Table 2.

TABLE 2

Preparation of 1,1,1,3,3-pentafluoropropane

| Reaction T (° C.) | Lights | % Selectivity CF$_3$CH$_2$CF$_2$H | Heavies |
|---|---|---|---|
| 50 | 2.7 | 94.4 | 2.9 |
| 35 | 2.6 | 95.0 | 2.4 |

While the invention has been described in detail in the foregoing description, the same is to be considered as illustrative and not restrictive in character, it being understood that only the preferred embodiment has been described and that all changes and modifications that come within the spirit of the invention are desired to be protected.

What is claimed is:

1. A method for the production of 1,1,1,3,3-pentafluoropropene which comprises contacting 2,2-dichloro-1,1,1,3,3,3-hexafluoropropane with hydrogen in the presence of a metal-containing catalyst carried by a carbon support, at a temperature in the range of about 350° C. to about 800° C., and recovering the 1,1,1,3,3-pentafluoropropene from the resulting reaction product, wherein the metal-containing catalyst carried by a carbon support is selected from the group consisting of a metal, metal halide, metal oxide, metal oxyhalide and combinations thereof, wherein the metal of the catalyst is selected from the group consisting of Fe, Cu, Ni and Cr.

2. The method of claim 1, wherein the carbon catalyst support is activated carbon.

3. The method of claim 1, wherein said contacting is carried out in a reactor for a period of time between about 0.1 and 60 seconds.

4. The method of claim 1, wherein the molar ratio of hydrogen to 2,2-dichloro-1,1,1,3,3,3-hexafluoropropane is between about 0.1 and about 30.

5. The method of claim 4, wherein the molar ratio of hydrogen to 2,2-dichloro-1,1,1,3,3,3-hexafluoropropane is between about 2 to 8.

6. The method of claim 1, wherein the reaction temperature is from about 350° C. to about 500° C.

7. The method of claim 1, wherein the reaction pressure is in the range from ambient to about 450 psi.

8. The method of claim 7, wherein the reaction pressure is in the range of ambient to about 200 psi.

9. A method for the production of 1,1,1,3,3-pentafluoropropane comprising (1) contacting 2,2-dichloro-1,1,1,3,3,3-hexafluoropropane with hydrogen in the presence of a metal-containing catalyst carried by a carbon support, at a temperature in the range of about 350° C. to about 800°C., and recovering 1,1,1,3,3-pentafluoropropene from the resulting reaction product, wherein the metal-containing catalyst carried by a carbon support is selected from the group consisting of a metal, metal halide, metal oxide, metal oxyhalide and combinations thereof, wherein the metal of the catalyst is selected from the group consisting of Fe, Cu, Ni and Cr, and (2) contacting the recovered 1,1,1,3,3-pentafluoropropene with hydrogen in the presence of a metal-containing catalyst to produce 1,1,1,3,3-pentafluoropropane.

10. The method of claim 9, wherein the metal-containing catalyst is selected from the group consisting of a metal, metal halide, metal oxide, metal oxyhalide and combinations thereof.

11. The method of claim 10, wherein the carbon catalyst support is activated carbon.

12. The method of claim 9, wherein the molar ratio of hydrogen to 2,2,-dichloro-1,1,1,3,3,3-hexafluoropropane is between 0.1 and about 30.

13. The method of claim 9, wherein the molar ratio of hydrogen to 2,2-dichloro-1,1,1,3,3,3-hexafluoropropane is between 2 to 8.

14. The method of claim 9, wherein the reaction temperature is from about 350° C. to about 500° C. and the pressure is from ambient to about 450 psi.

15. A method for the production of 1,1,1,3,3-pentafluoropropene, with a selectivity of at least 80%, which comprises contacting 2,2-dichloro-1,1,1,3,3,3-hexafluoropropane with hydrogen in the presence of a metal-containing catalyst carried by a carbon support, at a temperature in the range of about 350° C. to about 800° C., and recovering the 1,1,1,3,3-pentafluoropropene from the resulting reaction product, wherein the metal-containing catalyst carried by a carbon support is selected from the group consisting of a metal, metal halide, metal oxide, metal oxyhalide and combinations thereof, wherein the metal of the catalyst is selected from the group consisting of Cu, Ni.

16. The method of claim 15, wherein the carbon catalyst support is activated carbon.

17. The method of claim 15, wherein said contacting is carried out in a reactor for a period of time between about 0.1 and 60 seconds.

18. The method of claim 15, wherein the molar ratio of hydrogen to 2,2-dichloro-1,1,1,3,3,3-hexafluoropropane is between about 0.1 and about 30.

19. The method of claim 18, wherein the molar ratio of hydrogen to 2,2-dichloro-1,1,1,3,3,3-hexafluoropropane is between about 2 to 8.

20. The method of claim 15, wherein the reaction temperature is from about 350° C. to about 500° C.

21. The method of claim 15, wherein the reaction pressure is in the range from ambient to about 450 psi.

22. The method of claim 21, wherein the reaction pressure is in the range of ambient to about 200 psi.

23. The method of claim 15, wherein the selectivity is in the range of 80–90%.

24. A method for the production of 1,1,1,3,3-pentafluoropropane, with a selectivity of at least 75.52%, comprising (1) contacting 2,2-dichloro-1,1,1,3,3,3-hexafluoropropane with hydrogen in the presence of a metal-containing catalyst carried by a carbon support, at a temperature in the range of about 350° C. to about 800° C., and recovering 1,1,1,3,3-pentafluoropropene from the resulting reaction product, wherein the metal-containing catalyst carried by a carbon support is selected from the group consisting of a metal, metal halide, metal oxide, metal oxyhalide and combinations thereof, wherein the metal of the catalyst is selected from the group consisting of Fe, Cu, Ni and Cr, and (2) contacting the recovered 1,1,1,3,3-pentafluoropropene with hydrogen in the presence of a metal-containing catalyst to produce 1,1,1,3,3-pentafluoropropane.

25. The method of claim 24, wherein the metal-containing catalyst is selected from the group consisting of a metal, metal halide, metal oxide, metal oxyhalide and combinations thereof.

26. The method of claim 25, wherein the carbon catalyst support is activated carbon.

27. The method of claim 24, wherein the reaction temperature is from about 350° C. to about 500° C.

* * * * *